United States Patent
Smith et al.

(10) Patent No.: US 7,507,578 B2
(45) Date of Patent: Mar. 24, 2009

(54) REDUCED APERTURE BIOLOGICAL SPECIMEN COLLECTION AND TRANSFER DEVICE

(75) Inventors: Arthur L. Smith, Tyngsboro, MA (US); Mark Wladkowski, Groveland, MA (US); Albert Wright, Dunstable, MA (US)

(73) Assignee: Cytyc Corporation, Marlborough, MA (US)

(*) Notice: Subject to any disclaimer, the term of this patent is extended or adjusted under 35 U.S.C. 154(b) by 707 days.

(21) Appl. No.: 10/971,843

(22) Filed: Oct. 21, 2004

(65) Prior Publication Data

US 2006/0088930 A1 Apr. 27, 2006

(51) Int. Cl.
*C12M 1/12* (2006.01)

(52) U.S. Cl. .............. 435/295.3; 435/287.9; 435/297.2; 435/309.1; 435/309.4; 422/74; 422/99; 422/101; 73/61.71; 73/864.72

(58) Field of Classification Search ........... 73/61.71, 73/864.72; 422/74; 435/295.3, 297.2, 297.5, 435/309.4

See application file for complete search history.

(56) References Cited

U.S. PATENT DOCUMENTS

| | | | |
|---|---|---|---|
| 2,276,841 A | | 3/1942 | Hanson |
| 4,357,240 A | * | 11/1982 | Mehra et al. ............... 210/455 |
| 4,485,015 A | * | 11/1984 | Smith ........................ 210/455 |
| 5,077,012 A | * | 12/1991 | Guirguis ..................... 422/58 |
| 5,143,627 A | | 9/1992 | Lapidus et al. |
| 5,364,597 A | | 11/1994 | Polk, Jr. et al. |
| 5,372,447 A | * | 12/1994 | Chung ....................... 403/171 |
| 5,503,802 A | * | 4/1996 | Polk et al. .................. 422/101 |
| 5,772,818 A | | 6/1998 | Polk, Jr. et al. |
| 6,318,190 B1 | | 11/2001 | Radcliffe et al. |

(Continued)

FOREIGN PATENT DOCUMENTS

EP 1455187 A1 9/2004

(Continued)

OTHER PUBLICATIONS

PCT International Search Report for PCT/US2005/036320, Applicant: Cytyc Corporation, Forms PCT/ISA/210 and 220, dated Mar. 21, 2005 (6 pages).

(Continued)

*Primary Examiner*—William H Beisner
*Assistant Examiner*—Michael Hobbs
(74) *Attorney, Agent, or Firm*—Vista IP Law Group, LLP (57) ABSTRACT

A filtration based biological specimen collection and transfer device is provided. The filtration and transfer device comprises a tubular body with two axial ends, an annular flange disposed at one of the axial ends, and a biological specimen filter affixed to the outer surface of the annular flange. Preferably, the annular flange has disposed on its outer surface an annular ridge having a uniform height and forming a planar rim upon which the filter sits. Optionally, the annular flange comprises two mounting portions and the filter is bonded to each of those mounting portions. A method of collecting microscopic biological particles carried in a fluid is provided using the filtration and transfer device and a method of manufacturing the filtration and transfer device are also provided. A filtration based biological specimen collection and transfer system using the filtration and transfer device and a kit for use with filtration based biological specimen collection and transfer systems are also provided.

9 Claims, 6 Drawing Sheets

U.S. PATENT DOCUMENTS

| | | | |
|---|---|---|---|
| 6,372,447 B1* | 4/2002 | Raz | 435/30 |
| 6,572,824 B1 | 6/2003 | Ostgaard et al. | |
| 6,884,341 B2* | 4/2005 | Ferguson | 210/132 |
| 2003/0098271 A1 | 5/2003 | Somack et al. | |
| 2004/0063169 A1* | 4/2004 | Kane | 435/30 |

FOREIGN PATENT DOCUMENTS

| | | |
|---|---|---|
| WO | WO 86/07606 | 12/1986 |
| WO | WO 00/46597 | 8/2000 |

OTHER PUBLICATIONS

PCT Written Opinion of the International Search Aurthority for PCT/US2005/036320, Applicant: Cytyc Corporation, Form PCT/ISA/237, dated Mar. 2005 (5 pages).

PCT International Prelilminary Report on Patentability PCT/US2005/036320, Applicant CYTYC Corporation, forms PCT/IB/326, PCT/IB/373 and PCT/ISA/237 dated May 3, 2007 (7 pages).

Chinese Office Action for related application No. 200580036136.7, dated Sep. 19, 2008, Applicant Cytyc Corporation and translation provided by foreign associate (11 pages).

* cited by examiner

REDUCED APERTURE BIOLOGICAL SPECIMEN COLLECTION AND TRANSFER DEVICE

FIELD OF THE INVENTION

The present inventions generally relate to devices for collecting and transferring microscopic particles to prepare biological specimens.

BACKGROUND OF THE INVENTION

Many medical tests, including pap smears, require a physician to collect cells by brushing and/or scraping a skin or mucous membrane in a target area with an instrument. The cells are then smeared onto a slide, and are fixed and transported to a laboratory where the slide is stained. The slide can then be examined under a microscope by a cytotechnologist and/or a pathologist to identify cellular abnormalities. During evaluation, a pathologist may employ a polychrome technique, characterized by staining the nuclear part of the cells, to determine the presence of dysplasia or neoplasia. The pathologist may also apply a counter-stain for viewing the cytoplasm of the cells. Because the sample may contain debris, blood, mucus, and other obscuring artifacts, the test may be difficult to evaluate, and may not provide an accurate diagnostic assessment of the collected sample.

Cytology based on the collection of the exfoliated cells into a liquid preservative offers many advantages over the traditional method of smearing the cells directly onto the slide. A slide can be prepared from the cell suspension using a filter transfer technique, as disclosed in U.S. Pat. Nos. 6,572,824, 6,318,190, 5,772,818, 5,364,597, and 5,143,627, which are expressly incorporated herein by reference.

Filter transfer methods generally start with a collection of cells suspended in a liquid. These cells may be collected and dispersed into a liquid preservative or they may naturally exist in a collected biological liquid. Dispersion in liquid preservatives containing methanol, such as PreservCyt™ solution, breaks up mucus and lyses red blood cells and inflammatory cells, without affecting the cells of interest. The liquid is then passed through a filter with a fixed diameter aperture covered by a membrane to concentrate and collect the cells. Debris, such as lysed blood cells and dispersed mucus, which flow through the pores of the membrane, are not collected on the membrane and are greatly reduced by the combined method of dispersion and filtering. Then the cells collected on the membrane are transferred onto a slide.

Existing filter transfer methods use filters with a fixed diameter aperture. Therefore cell samples spots are of a uniform size, i.e., 21 mm, even when smaller spots, i.e., 7 mm, are desired for a specific test. A prior device for collecting a dispersed monolayer of cells, and for transferring them to a microscope slide for examination, has a tube with a filter-positioning rim with a highly planar geometry to position a filter for transferring collected cells to the microscope slide with faithful retention of the spatial distribution of the collected particles. The equipment for manufacturing and using this device is standardized based on the diameter of the tube on which the filter is fixed.

It has been found that adjusting the aperture of this known filter device of the type described above without changing the diameter of the tube leads to microfluid dynamic effects that distort the spatial distribution of the collected particles upon transfer. Methods of adjusting the aperture include the use of a Mylar® ring on the underside of the filter and use of a membrane with open and closed areas.

Consequently, existing filter transfer methods use filters with uniform apertures and may result in excess cells being transferred and subsequently discarded. These excess cells require the use of extra test reagents, leading to increased costs. Reducing the amount of cells lost while forming a cell sample not only reduces the amount of test reagent used, but also increases the number of tests that can be performed on cells retrieved during one sample collection procedure. This in turn allows for more confirmation testing, conserves difficult to collect cells, and reduces the number times a patient would be subjected to a collection procedure.

Accordingly, there exists a need for a device and method for forming samples of varying specific sizes using filter transfer methods. There also exists a need for a device and method for forming samples of varying specific sizes while maintaining a standard tube size and faithful retention of the spatial distribution of the collected particles.

SUMMARY OF THE INVENTION

In accordance with a first aspect of the present inventions, a filtration based biological specimen collection and transfer device is provided. The filtration and transfer device comprises a tubular body with two axial ends, an annular flange disposed at one of the axial ends, and a biological specimen filter affixed to the outer surface of the annular flange. Preferably, the annular flange has disposed on its outer surface an annular ridge having a uniform height and forming a planar rim upon which the filter sits. The annular flange preferably also has disposed on its outer surface two annular troughs used in bonding the filter to the flange.

Optionally, the annular flange comprises two mounting portions and the filter is bonded to each of those mounting portions. Also optionally, the filter comprises a filter portion and a mounting portion radially outwardly of the filter portion, which is bonded to the two mounting portions on the annular flange. The filtration and transfer device optionally comprises a cap, which fluidly closes the axial end of the tubular body opposite of the axial end at which the annular flange is disposed. Further, the filtration and transfer device optionally comprises a pneumatic source conduit and a pressure monitor conduit, which are respectively connect to a pneumatic source and a pressure monitor.

In accordance with another aspect of the present inventions, a method of collecting microscopic biological particles carried in a fluid is provided. The method comprises positioning the above-described filtration and transfer device in a fluid carrying microscopic biological particles, and applying a vacuum to draw the fluid into the device and to collect the biological particles on the filter.

In accordance with another aspect of the present inventions, a filtration based biological specimen collection and transfer system is provided. The collection and transfer system comprises a tubular body with two axial ends, an annular flange disposed at one of the axial ends, and a biological specimen filter affixed to the outer surface of the annular flange. The system further comprises a pneumatic source connected to the tubular body via a pneumatic source conduit and a pressure monitor connected to the tubular body via a pressure monitor conduit. Preferably, the annular flange has disposed on its outer surface an annular ridge having a uniform height and forming a planar rim upon which the filter sits. The annular flange preferably also has disposed on its outer surface two annular troughs used in bonding the filter to the flange.

Optionally, the annular flange comprises two mounting portions and the filter is bonded to each of those mounting portions. Also optionally, the filter comprises a filter portion and a mounting portion radially outwardly of the filter portion, which is bonded to the two mounting portions on the annular flange. The filtration and transfer system optionally comprises a cap, which fluidly closes the axial end of the tubular body opposite of the axial end at which the annular flange is disposed.

In accordance with still another aspect of the present invention, a kit for use with filtration based biological specimen collection and transfer systems is provided. The kit comprises a first tubular body with two axial ends, a first annular flange, which defines a first opening, disposed at one of the axial ends, and a first biological specimen filter affixed to the outer surface of the first annular flange. The kit further comprises a second tubular body with two axial ends, a second annular flange, which defines a second opening, disposed at one of the axial ends, and a second biological specimen filter affixed to the outer surface of the second annular flange. The first and second openings have different apertures.

In accordance with yet another aspect of the present invention, a method of manufacturing a filtration based biological specimen collection and transfer device is provided. The method comprises bonding a biological specimen filter to an annular flange disposed at an axial end of a tubular body, heat-shrinking the filter, and bonding the filter to the annular flange a second time. The bonding preferably takes place thermally or ultrasonically.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
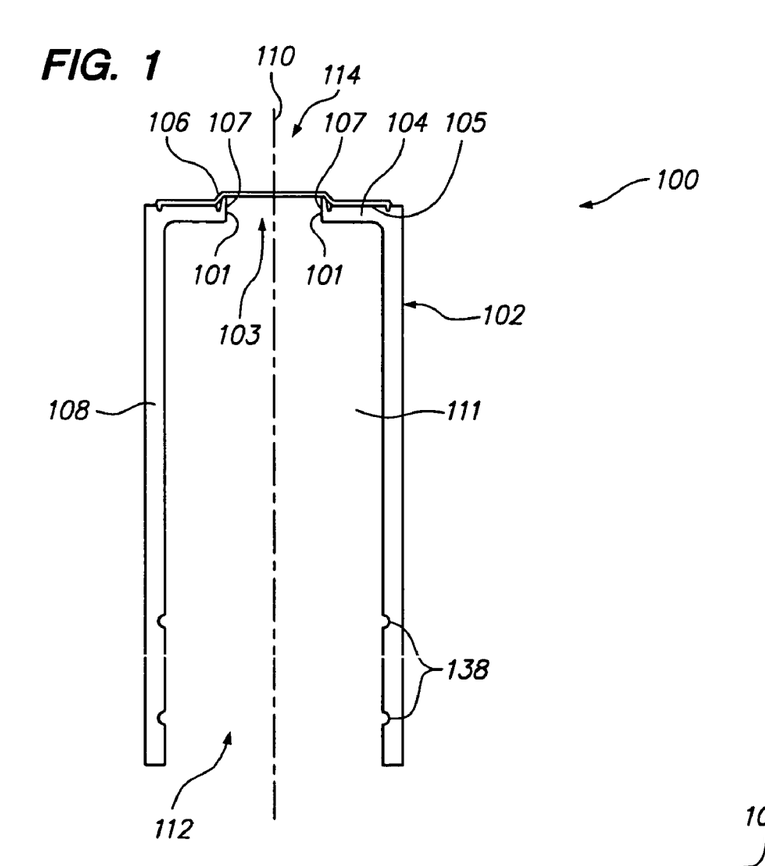
FIG. 1 is a side sectional view of a biological specimen filtration and transfer device constructed in accordance with a preferred embodiment of the present invention.

Referring to FIG. 1, a preferred embodiment of a biological specimen filter device 100 will now be described. As will be described in further detail below, the filter device 100 can be used with a biological specimen collection and transfer system 166 (FIG. 7), which is designed for transferring a biological specimen from a sample collection container 168 to a biological specimen slide 132 (shown in FIG. 4) using a filtration technique. To this end, the filter device 100 generally comprises a tubular body 102, an annular flange 104 disposed at one end of the tubular body 102, and a biological specimen filter membrane 106 affixed to the annular flange 104.

The tubular body 102 is formed of a cylindrical wall 108 that extends along a longitudinal axis 110. The cylindrical wall 108 terminates at a proximal axial end 112 that is completely open, and at a distal axial end 114 in the annular flange 104. The annular flange 104 comprises a radially inward facing surface 101 that defines a central aperture 103 in communication with a vacuum cavity 111 defined by the tubular body 102. In the illustrated embodiment, the tubular body 102 and annular flange 104 are molded as a single piece, from polystyrene resin marketed by the Dow Chemical Company under the designation Styron 685D. Consequently, there are no seams between these parts that may leak under pressure during use of the filter device 100. Alternatively, however, the tubular body 102 and annular flange 104 may be initially formed of separate pieces and then bonded together.

The annular flange 104 comprises an exterior mounting surface 105 to which the filter membrane 106 is mounted. When mounted to the annular flange 104, the filter membrane 106 comprises an annular peripheral portion 136 that coincides with the annular flange 104, and a central aperture portion 126 that coincides with and spans across the central aperture 103 formed at the distal end 114 of the tubular body 102. As will be described in further detail below, particulate may be captured on the central filter aperture portion 126 while the solution that contains the particulate flows therethrough. To this end, the filter membrane 106 takes the form of a porous polycarbonate membrane treated with a wetting agent, as commercially available from manufacturers to be hydrophilic. In the illustrated embodiment, filter membrane 106 is on the order of sixteen microns thick, and is available from Whatman Corporation, Stanford, Me. 04024.

The filter membrane 106 may be mounted to the mounting surface 105 of the annular flange 104 in any suitable manner, but in the illustrated embodiment, is heat bonded thereto, as will be described in greater detail below. Alternatively, the filter membrane 106 can also be ultrasonically bonded to the mounting surface 105 of the annular flange 104. A suitable ultrasonic bonding process is available from. Polyfiltronics, Inc. of Rockland, Mass. 02370. The filter membrane 106 may also be solvent bonded to the mounting surface 105 of the annular flange 104 as well.

Figure 7:
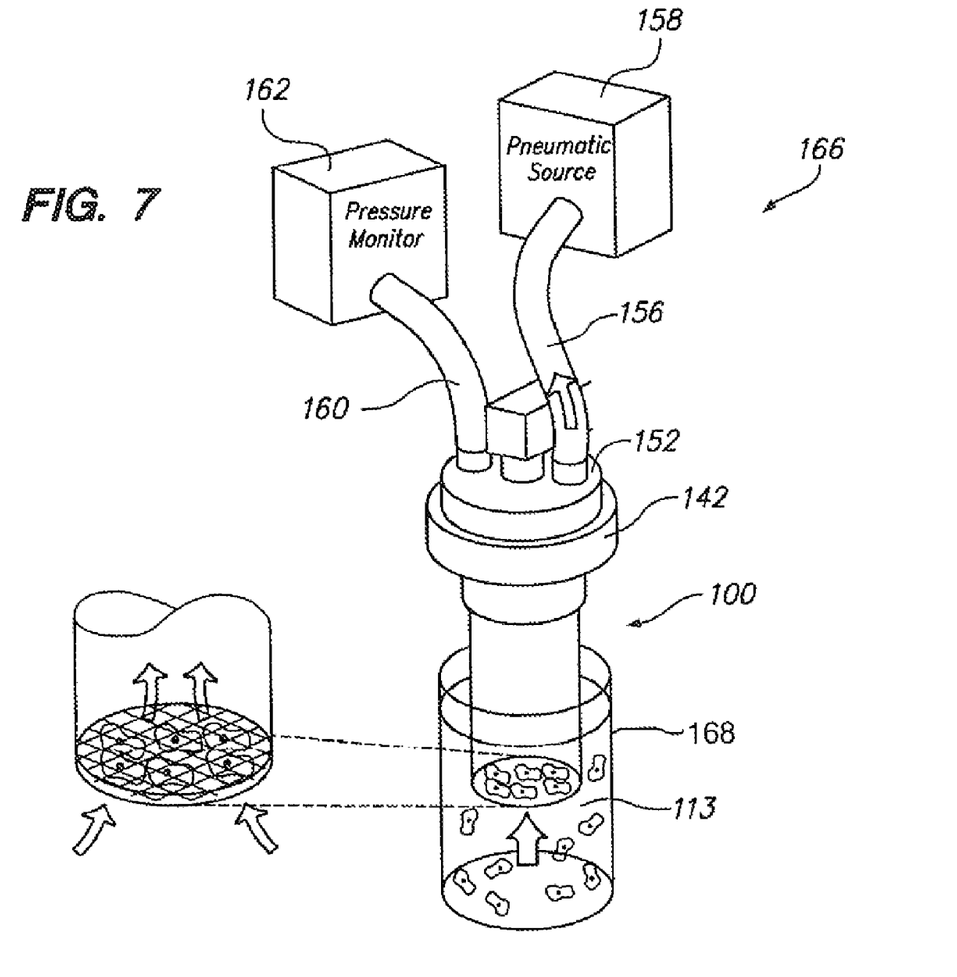
FIG. 7 is a perspective view of a biological specimen filtration and transfer system in accordance with a preferred embodiment of the present invention.
Figure 8:
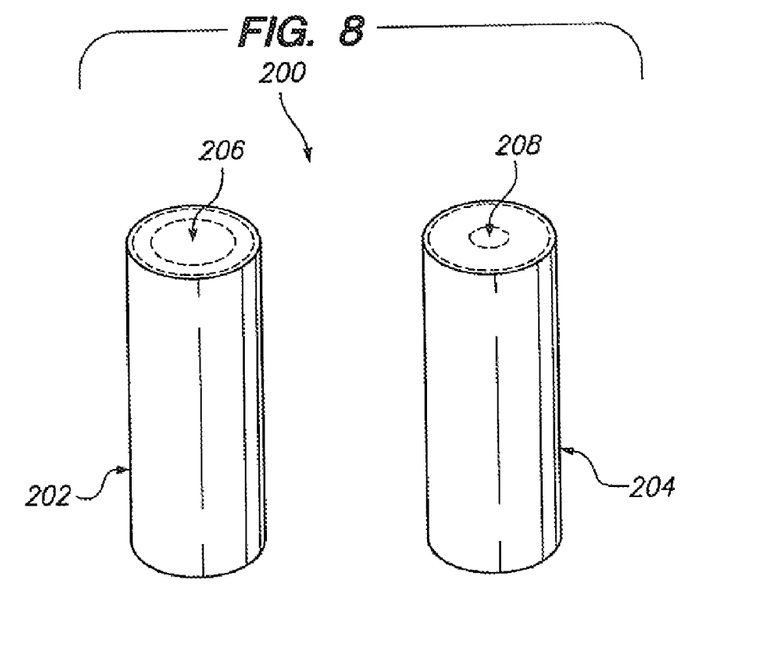
FIG. 8 is a perspective view of two biological specimen filtration and transfer devices constructed in accordance with a preferred embodiment of the present invention.

Thus, it can be appreciated that the annular flange 104 allows the diameter of the central filter aperture portion 126 to be reduced while the diameter of the tubular body 102 remains the same. Further, a biological specimen filtration and transfer kit 200 can be assembled from two or more tubular bodies 202/204 having different apertures 206/208, as shown in FIG. 8. The tubular bodies 206/208 are configured to be closed by the same cap 142 (see FIG. 5) and to be used interchangeably in a biological specimen collection and transfer system 166 (see FIG. 7).

Figure 2:
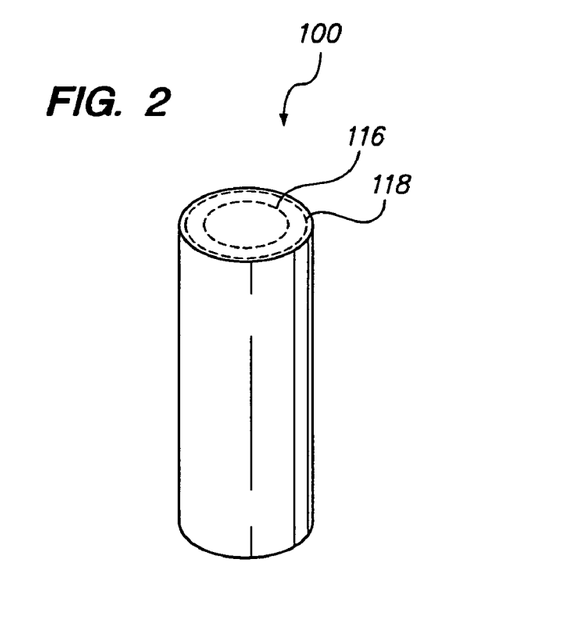
FIG. 2 is a perspective view of the filtration and transfer device of the FIG. 1.
Figure 3:
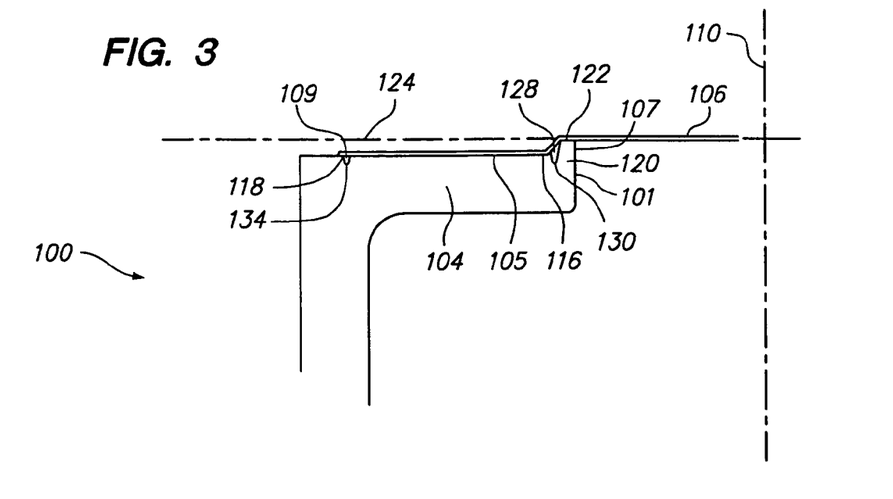
FIG. 3 is a detailed side sectional view of the filtration and transfer device of the FIG. 1.

Referring now to FIGS. 2 and 3, the annular flange 104 comprises several features that enhance the efficacy of the filtering device 100. In particular, the annular flange 104 comprises an annular ridge 120 disposed radially inward from the mounting surface 116. The annular ridge 120 features a distal positioning rim 122 across which the filter membrane 106 is stretched. So that the central filter region 126 takes on a highly planar geometry, the positioning rim 122 lies in a plane 124 approximately perpendicular to the longitudinal axis 110, and the annular ridge 120 is of a uniform height. In the illustrated embodiment, the annular ridge 120 comprises a radially inward facing ridge surface 107 that is flush with the radially inward facing surface 101 of the annular flange 104. Alternatively, the radially inward facing ridge surface 107 may be offset radially outward from the radially inward facing flange surface 101.

As shown in FIG. 3, the mounting surface 105 is topologically divided into an inner annular mounting surface 116 and an outer annular mounting surface 118, which are in a concentric relationship with each other. As will be discussed in further detail below, the use of mounting surfaces 116/118 allows the filter membrane 106 to be advantageously mounted to the annular flange 104 in incremental steps. The annular flange 104 further comprises an inner annular air barrier 128 that is concentric with and radially interposed between the ridge 120 and the inner mounting surface 116. The illustrated barrier 128 takes the form of an inner annular trough 130, which presents a thermal barrier that isolates any heat developed at the mounting surface 105 during heat bonding of the filter membrane 106, thereby minimizing distortion, or otherwise geometric alteration, of the positioning rim 122. If solvent bonding is used to mount the filter membrane 106 to the annular flange 104, the barrier 128 also retards the solvent action from deforming the rim 122. Further, the barrier 128 provides a receptacle for trapping and otherwise receiving debris and other excess or flowing material produced during the bonding or other attachment of the filter membrane 106 to the inner mounting surface 116. Thus, the barrier 128 substantially isolates the positioning rim 122 from distortion and from material debris that might otherwise alter or detract from the desired highly planar surface which the positioning rim 122 defines.

Figure 4:
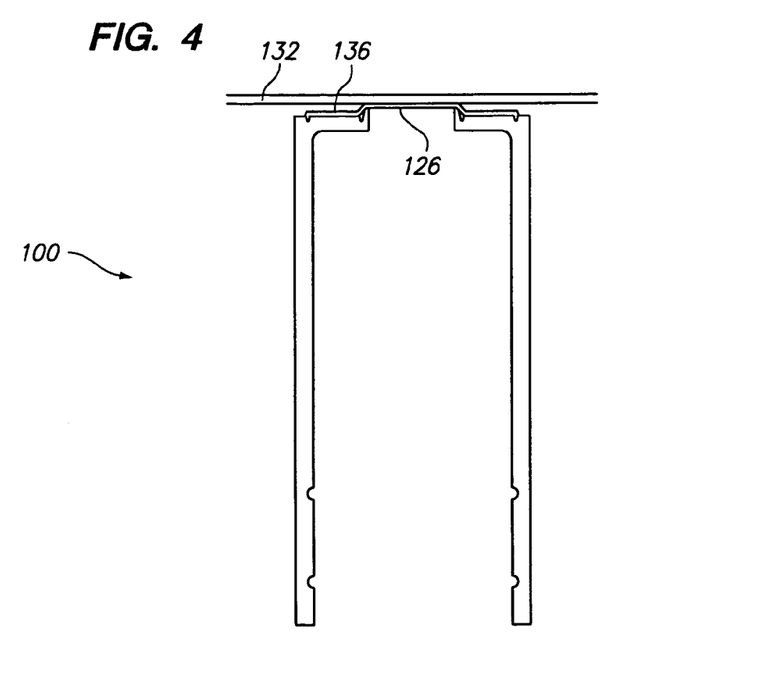
FIG. 4 is a side sectional view of the filtration and transfer device of the FIG. 1 adjacent to a microscope slide.

Thus, it can be appreciated that distortions of the mounting surface 105 caused by mounting of the filter membrane 106 do not alter the precise positioning geometry of the positioning rim 122. As a result, the central filter region 126 can have a precise planar disposition. Thus, when a biological specimen slide 132, such as a microscope slide, is brought into contact with the central filter region 126, as shown in FIG. 4, the entire central filter region 126 abuts the support device 132 in a flush manner. This substantially uniform abutment enables collected particles located on the entire surface of the central filter region 126 to be transferred directly to the support device 132. As a result, the particles will be transferred to the specimen slide 132 with the same spatial distribution that they had on the filter membrane 106, while also minimizing the amount of particles remaining on the filter membrane 106 after transfer.

The annular flange 104 also features an outer annular air barrier 109 that is interposed between the inner and outer mounting surfaces 116/118. In the same manner described above with respect to the inner annular air barrier 128, the outer annular barrier 109 takes the form of an annular trough that provides a receptacle for trapping and otherwise receiving debris and other excess or flowing material produced during the bonding or other attachment of the filter membrane 106 to the outer mounting surface 118.

As briefly discussed above, one preferred method of mounting the filter membrane 106 to the annular flange 104 involves heat bonding. In this process, a first thermal bonding step, wherein the filter membrane 106 is welded by heat to the outer mounting surface 118 on the flange 104 is initially performed. Then, a filter-shrinking step, which uniformly tensions the filter membrane 106 to enhance the flat, wrinkle-free disposition of the filter membrane 106 on the flange 104, is performed. As previously described above, it has been found that the transfer of particles from the collection filter membrane 106 to the specimen slide 132 is enhanced by performing this filter-shrinking step, preferably after the first step of thermally bonding the filter membrane 106 to the outer mounting surface 118 of the flange 104. Finally, to prevent hydrodynamic effects from interfering with the transfer of the filtered particles, a third step of thermal bonding, wherein the filter membrane 106 is welded by heat to the inner mounting surface 116 on the flange 104 is employed.

Figure 9:
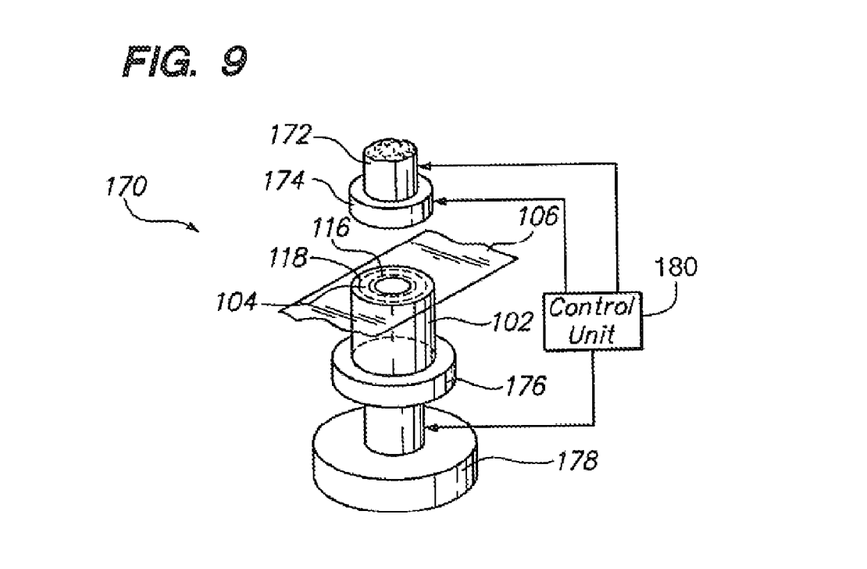
FIG. 9 is a schematic representation of a process for fabricating a biological specimen filtration and transfer device in accordance with a preferred embodiment of the present invention.

FIG. 9 illustrates a thermal-bonding apparatus 170 used to mount the filter membrane 106 to the annular flange 104 by way of a thermal-bonding process. The fabrication apparatus 170 is essentially an arbor press with a heated ram 172 having a ram tip 174. The ram tip 174, which is shaped like a horn or hollow tube having approximately the same diameter as an outer annular mounting surface 118 of the flange 104, is pressed directly against the filter membrane 106 and is maintained at a temperature capable of welding the filter membrane 106, and preferably the peripheral region 136 of the filter membrane 106, to the flange 104. The ram tip temperature preferably is controlled, for instance, with digital control to obtain ±1° F. accuracy.

The contact pressure between the ram tip 174, the filter membrane 106, and the flange 104 is controlled, in the illustrated equipment, by supporting the tubular body 102 on an air cylinder 176 mounted on a press base 178. The ram 172 is lowered until it engages a stop. The air cylinder 176 on the base 178 then takes up the load. The load can be set by varying the pressure to the air cylinder 176. The dwell time of the bonding step, i.e., the time the ram tip 174 remains pressed against the filter membrane 106 and flange 104, can be controlled by timing and reversing the direction of the air cylinder 176 to remove the load and heat on the flange 104 and filter membrane 106. For instance, a limit switch (not shown) can activate a timer when the arbor ram 172 hits a stop, to determine the dwell time of the ram tip 174 against the filter membrane 106 and flange 104.

The apparatus 170 comprises a control unit 180 that provides control of the ram tip temperature, compression force and dwell time. The control unit 180 is preferably driven by a microprocessor, with connections to a pressure sensing unit in the air cylinder 176, a temperature sensing unit in the ram tip 174 and a microswitch activated by the ram 172 engaging its stop. A control unit 170 for this purpose can be provided by those skilled in the art using known techniques.

Upon lowering of the ram 170 and engagement of the stop, the control unit 180 actuates a pneumatic pump or compressed air source connected to the air cylinder 176. The control unit 180 monitors and adjusts the pressure to the air cylinder 176 such that it matches the desired compression force when the ram tip 174 is contacted by the filter membrane 106 and flange 104. The dwell time of this contact is determined relative to the contacting of the stop by the ram 172, or alternatively, it can be relative to the achievement of a set pressure value in the air cylinder 176. At the end of the predetermined dwell time, the control unit 180 releases the pressure in the air cylinder 176, thus removing the flange 104 and filter membrane 106 from the ram tip 174. The control unit 180 senses and adjusts the temperature of the ram 172 and ram tip 174 such that the desired ram tip temperature in maintained to within ±1° F.

The operating conditions for the thermal bonding step includes determining temperature, the dwell time, and the bonding force or pressure. For instance, increasing the temperature of the ram 172 can generally be offset by decreasing the dwell time and the compression force, and vice-versa. The process is considered optimal when the flange melt is minimal, the wetting of the flange/filter interface is even, and the mechanical strength of the filter membrane 106 bond to the flange 104 is high. When the temperature, dwell time and load force parameters are too great, the result can be unwanted deformation of the flange 104. Conversely, when these parameters are too small, the resulting bond is weak and the filter membrane 106 delaminates more easily from the flange 104. One particularly useful test of these process conditions comes from determining the quality of a slide produced by the deposition of sample material from the filter membrane 106 by the filter device 100.

After the filter membrane 106 is attached to the outer mounting surface 118, the filter membrane 106 is trimmed to approximate the diameter of the flange 104. This eliminates excess filter material which might interfere with the particle collection and transfer process.

As previously discussed above, the filter membrane 106 is composed of a polycarbonate, and the tubular body 102 and flange 104 are composed of polystyrene. The process parameters for the mechanical bonding of the polycarbonate filter membrane 106 to the polystyrene flange 104 in the manner described above with the equipment of FIG. 9, are as follows:

| | |
|---|---|
| Ram Tip Temperature: | 275-350° F. |
| Compression Force: | 20-60 lbs |
| Dwell Time: | 0.75 to 2.0 seconds |
| Ram Tip Configuration | |
| Outer Dia.: | 1.0 in |
| Inner Dia.: | 0.89 in |

The melting point of polycarbonate is higher than that of polystyrene, and therefore under these conditions, the heat from the ram tip 174, conducted through the filter membrane 106, causes the outer mounting surface 118 to melt and form a mechanical bond with the polycarbonate filter membrane 106. One specific preferred combination of parameters for the thermally induced mechanical bonding of the filter membrane 106 to the flange 104 is:

| | |
|---|---|
| Ram Tip Temperature: | 350° F. |
| Compression Force: | 40 lbs |
| Dwell Time: | 0.75 seconds |

Figure 10:
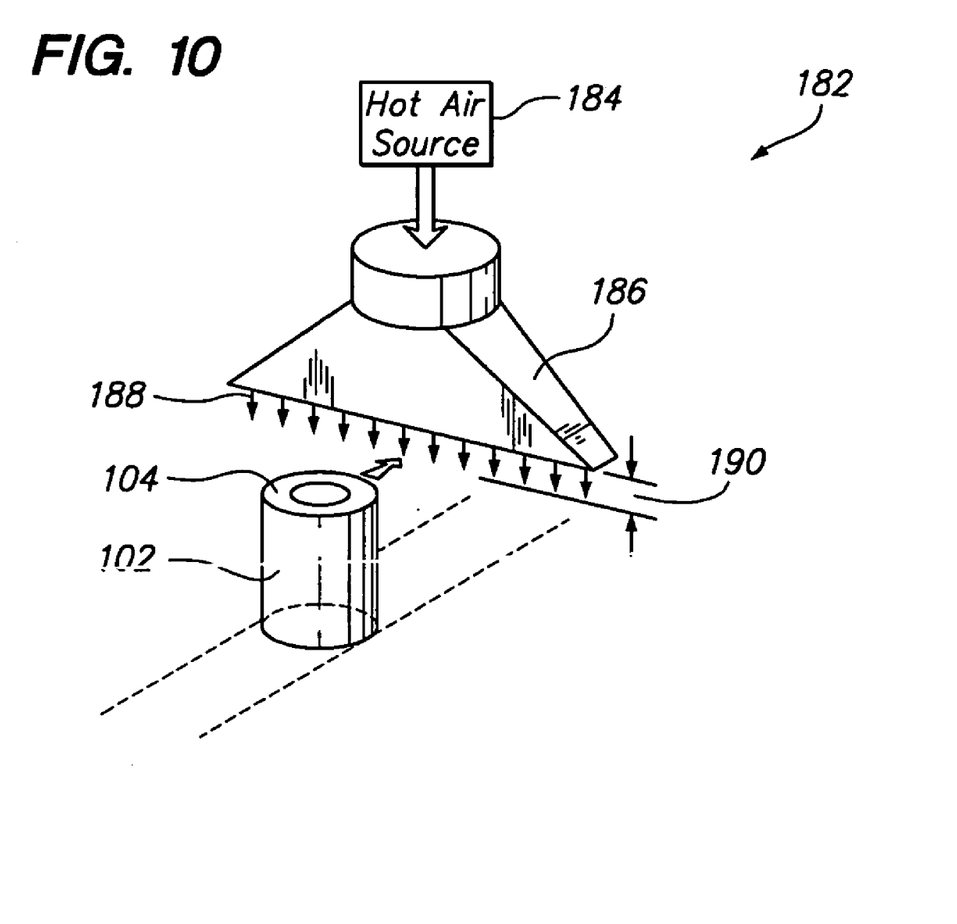
FIG. 10 is a schematic representation of a process for fabricating a biological specimen filtration and transfer device in accordance with a preferred embodiment of the present invention.

FIG. 10 illustrates a heat-shrinking apparatus 182 that can be used to perform the heat-shrinking step. The apparatus 182 comprises a variable temperature hot air source 184, and a flow-directing baffle 186 to direct a hot air flow 188 onto the filter membrane 106 secured on the flange 104. The tubular body 102, with the thermally bonded filter membrane 106 is passed under the flow-directing baffle 186 of the hot air source 184 at a controlled speed and a selected minimal spacing 190. The hot air temperature is maintained such that the filter membrane 106 contracts and is tensioned substantially uniformly in all directions. To vary the duration of heat application, the speed at which the tubular body 102 is passed through the heat flow 188 can be varied. The duration of heat exposure is inversely proportional to the speed at which the tubular body 102 is passed through the heat flow 188.

The process parameters for the heat-shrinking step carried out by the illustrated embodiment are:

| | |
|---|---|
| Air Temperature: | 250-400° F. |
| Duration of Heat Application (expressed in terms of cylinder speed): | 0.5 to 2.0 in/sec |

In one specific illustrative practice, the hot air source employed is a variable temperature hot air gun (Master Appliance, VariTemp Heat Gun VT 752C) and a flow directing baffle with output dimensions of 8 inches×0.2 inches. The air temperature is maintained at 400° F., and the tubular body 102 is passed through the heated air flow 326 at a speed of 1.3 inches per second. When the tubular body 102 is positioned directly beneath the flow directing baffle 324, the items are approximately 0.5 inches apart. Those skilled in the art will appreciate that other combinations of parameter values can be used.

The second filter bonding step thermally bonds the filter membrane 106 to the inner annular bonding surface 116, using the method as described above for the first filter bonding step, with one difference. The arbor ram (not shown) used in the second filter bonding step has a ram tip (not shown) has approximately the same diameter as the inner annular mounting surface 116 of the flange 104

Figure 5:
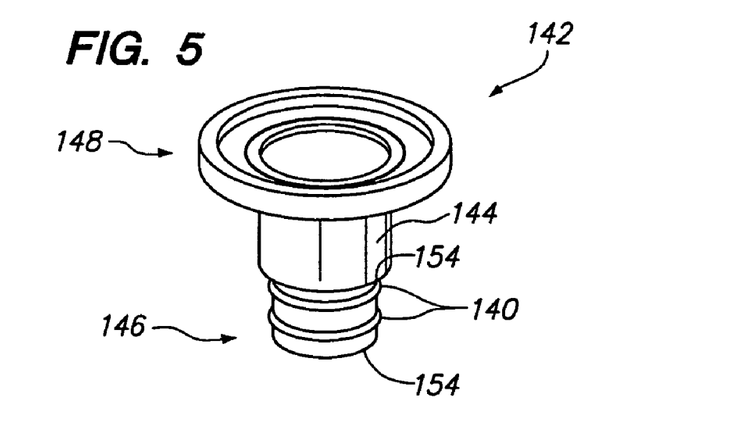
FIG. 5 is a perspective view of a cap configured for use with the filtration and transfer device of the FIG. 1.
Figure 6:
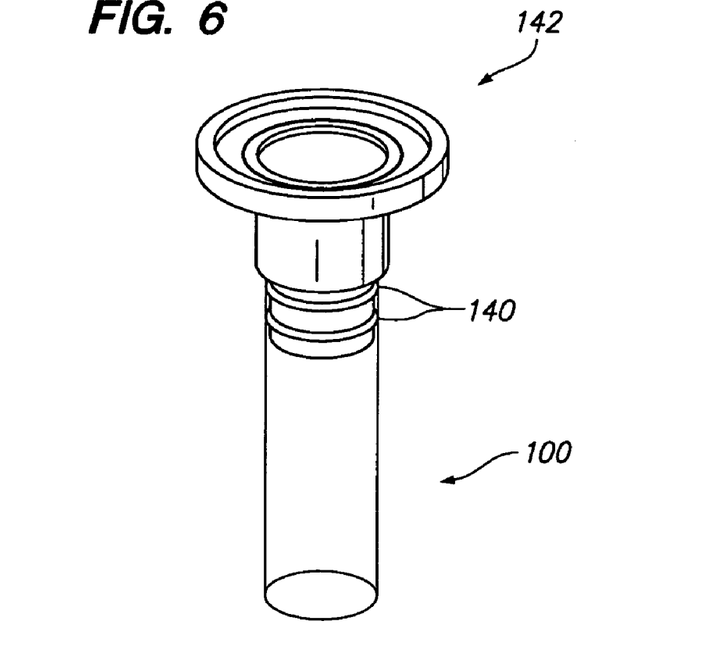
FIG. 6 is a perspective view of is a perspective view of a biological specimen filtration and transfer device constructed in accordance with a preferred embodiment of the present invention.

As shown in FIG. 6, the proximal end 112 of the filter device 100 is configured to tightly receive a removable cap 142. Referring further to FIG. 5, the cap 142 comprises a hollow cylinder 144 having a smaller male end 146 for insertion into the filter device 100, and an enlarged female end 148 for mating with a vacuum source (shown in FIG. 7). To facilitate the fluid tight attachment of the removable cap 142 with the filter device 100, the cap 142 comprises two annular recesses 154 formed within the outer surface of the male cap end 146, and two corresponding O-rings 140 that are received within the annular recesses 154. The O-rings 140 are composed of an elastic material, such as rubber, so that they can be secured within recesses 154. As shown in FIG. 1, two recesses are formed within the inner surface of the tubular body 102 at the proximal end 112, and are configured to tightly receive the O-rings 140 of the cap 142.

In order to mechanically interface with the filter device 100, the collection and transfer system 166 comprises a coupling mechanism 152 that mates with the cap 142 of the filter device 100. The collection and transfer system 166 also comprises two conduits 156 and 160, the distal ends of which extend through coupling mechanism 152 into fluid communication with the interior of the filter device 100. The proximal ends of the conduits 156 and 160 are connected to a pneumatic source 158 and a pressure monitor 162 of the collection and transfer system 166, respectively. In this manner, the pneumatic source 158 can apply negative pressure pulses to the interior of the filter device 100 via the conduit 156 in order to collect particles from the liquid sample 113. The pneumatic source 158 can also apply positive pressure pulses to the interior of the sample collection device 12 via the conduit 156 in order to dispense the collected particles onto the slide 132. The pressure monitor 162 allows the collection and transfer system 166 to more precisely control the pressure in the filter device 100.

For purposes of brevity in illustration and description, only the coupling mechanism 152, the conduits 156 and 160, the pneumatic source 158, and the pressure monitor 162 of the collection and transfer system 166 are shown. The structure and functionally of such types of collection and transfer systems are described in greater detail in U.S. Pat. Nos. 6,318, 190 and 6,572,824, which have previously been incorporated herein by reference.

As further described in the noted patents, the filtration and transfer device 100 with particles on the outer surface of the central filter region 126, after removal from the particle containing liquid, can be placed in abutment with the biological specimen support device 132, such as a microscope slide, as illustrated in FIG. 3. The cells or other particles collected on the filter membrane 106 are transferred to the support device 132. The transfer of particles from the filter membrane 106 to the support device 132 can be facilitated by applying an elevated pressure to the inner side of the 126.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A biological specimen filter device, comprising:
a tubular body having first and second axially disposed ends and an interior region comprising a vacuum cavity, the first end comprising a planar annular mounting surface disposed substantially orthogonal to a longitudinal axis of the tubular body, the mounting surface having an annular ridge extending therefrom away from the tubular body and surrounding an aperture in a central region of the first end, the aperture in fluid communication with, and having a smaller diameter than, the vacuum cavity; and
a filter membrane having a peripheral region affixed to the mounting surface, and a central region that spans across the aperture, wherein a surface of the central region facing away from the tubular body is raised away from the peripheral region by the ridge and configured to contact a planar sample transfer surface without the transfer surface contacting the peripheral region of the filter.

2. The filter device of claim 1, further comprising an annular air barrier interposed between the ridge and the mounting surface.

3. The filter device of claim 2, the air barrier comprising a depression formed in the first end surrounding the ridge.

4. The filter device of claim 1, wherein the filter membrane is configured for collecting thereon microscopic biological particles carried in a fluid.

5. A biological specimen filter device, comprising:
a tubular body having first and second axially disposed ends and an interior region comprising a vacuum cavity, the first end comprising a planar annular mounting surface disposed substantially orthogonal to a longitudinal axis of the tubular body, the mounting surface having an annular ridge extending therefrom away from the tubular body and surrounding an aperture in a central region of the first end, the aperture in fluid communication with, and having a smaller diameter than, the vacuum cavity, the first end further comprising a depression formed in the first end surrounding the ridge; and
a filter membrane configured for collecting thereon microscopic biological particles carried in a fluid and having a peripheral region affixed to the mounting surface, and a central region that spans across the aperture, wherein a surface of the central region facing away from the tubular body is raised away from the peripheral region by the ridge and configured to contact a planar sample transfer surface without the transfer surface contacting the peripheral region of the filter.

6. A biological specimen filter device, comprising:
a tubular body having first and second axially disposed ends and an interior region having a diameter defined by an inner wall of the tubular body, the first end comprising a planar annular mounting surface disposed substantially orthogonal to a longitudinal axis of the tubular body, the mounting surface having an annular ridge extending therefrom away from the tubular body and surrounding an aperture in a central region of the first end, the aperture in fluid communication with, and having a smaller than, the interior region of the tubular member; and
a filter membrane having a peripheral region affixed to the mounting surface, and a central region that spans across the aperture, wherein a surface of the central region facing away from the tubular body is raised away from the peripheral region by the ridge and configured to contact a planar sample transfer surface without the transfer surface contacting the peripheral region of the filter.

7. The filter device of claim 6, further comprising an annular air barrier interposed between the ridge and the mounting surface.

8. The filter device of claim 7, the air barrier comprising a depression formed in the first end surrounding the ridge.

9. The filter device of claim 6, wherein the filter membrane is configured for collecting thereon microscopic biological particles carried in a fluid.

* * * * *